US008653002B2

(12) United States Patent
Krapp et al.

(10) Patent No.: US 8,653,002 B2
(45) Date of Patent: Feb. 18, 2014

(54) AQUEOUS SUSPENSION CONCENTRATE FORMULATIONS CONTAINING SAFLUFENACIL

(75) Inventors: Michael Krapp, Altrip (DE); Wolfgang Gregori, Ludwigshafen (DE); Klaus Kolb, Schifferstadt (DE); Bernd Sievernich, Hassloch (DE); Heidi Emilia Saxell, Carlsberg (DE); Joerg Steuerwald, Boehl-Iggelheim (DE); Steven Bowe, Apex, NC (US); Rex Liebl, Raleigh, NC (US); Terrance M. Cannan, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/391,896

(22) PCT Filed: Aug. 26, 2010

(86) PCT No.: PCT/EP2010/062473
§ 371 (c)(1),
(2), (4) Date: Feb. 23, 2012

(87) PCT Pub. No.: WO2011/023759
PCT Pub. Date: Mar. 3, 2011

(65) Prior Publication Data
US 2012/0149577 A1 Jun. 14, 2012

Related U.S. Application Data

(60) Provisional application No. 61/237,406, filed on Aug. 27, 2009.

(51) Int. Cl.
*A01N 43/00* (2006.01)
*A01N 43/54* (2006.01)
*A01N 43/60* (2006.01)
*A01N 33/18* (2006.01)
*A61K 31/16* (2006.01)
*A61K 31/505* (2006.01)
*C07D 239/02* (2006.01)
*C07C 331/00* (2006.01)
*C07C 307/00* (2006.01)
*C07C 313/00* (2006.01)
*C07C 233/00* (2006.01)
*C07C 239/00* (2006.01)

(52) U.S. Cl.
USPC ........... 504/209; 504/235; 504/243; 504/326; 504/333; 504/337; 514/269; 514/274; 514/600; 514/603; 514/613; 544/312; 564/79; 564/86; 564/88; 564/101; 564/123; 564/163; 564/168

(58) Field of Classification Search
USPC ................. 504/209, 235, 243, 326, 333, 337; 514/269, 274, 600, 603, 613; 544/312; 564/79, 86, 88, 101, 123, 163, 168
See application file for complete search history.

(56) References Cited

U.S. PATENT DOCUMENTS

| | | | |
|---|---|---|---|
| 4,203,877 A * | 5/1980 | Baker | 524/500 |
| 6,479,432 B1 | 11/2002 | Sixl | |
| 8,362,026 B2 * | 1/2013 | Schmidt et al. | 514/274 |
| 2005/0159622 A1 | 7/2005 | Hamprecht et al. | |
| 2006/0293520 A1 | 12/2006 | Hamprecht et al. | |
| 2008/0293941 A1 | 11/2008 | Gebhardt et al. | |
| 2008/0318781 A1 | 12/2008 | Zagar et al. | |
| 2010/0105562 A1 | 4/2010 | Schmidt et al. | |
| 2012/0149577 A1 | 6/2012 | Krapp et al. | |
| 2012/0157312 A1 | 6/2012 | Krapp et al. | |
| 2012/0231954 A1 | 9/2012 | Krapp et al. | |

FOREIGN PATENT DOCUMENTS

| | | |
|---|---|---|
| EP | 0000424 | 1/1979 |
| WO | WO 01/22814 | 4/2001 |
| WO | WO 0130156 | 5/2001 |
| WO | WO 01/83459 | 11/2001 |
| WO | WO 03/024221 | 3/2003 |
| WO | WO 03/097589 | 11/2003 |
| WO | WO 2005/054208 | 6/2005 |
| WO | WO 2006/125746 | 11/2006 |
| WO | WO 2007/014758 | 2/2007 |
| WO | WO 2007/014759 | 2/2007 |
| WO | WO 2008/043835 | 4/2008 |
| WO | WO 2011023758 | 3/2011 |
| WO | WO 2011070051 | 6/2011 |
| WO | WO 2011070054 | 6/2011 |

OTHER PUBLICATIONS

English language translation of the International Preliminary Report on Patentability from corresponding International Application No. PCT/EP2010/062473, filed Aug. 26, 2012.
International Search Report in International Application No. PCT/EP2010/062473, filed Aug. 26, 2012.
Anonymous, "Kixor Herbicide Technical Brochure", BASF Agricultural Products, NC 27709, Jan. 2009, pp. 1-15 (XP000002651574), Search Report.
Office action dated Apr. 22, 2013, from U.S. Appl. No. 13/391,898.

* cited by examiner

*Primary Examiner* — Jane C Oswecki
(74) *Attorney, Agent, or Firm* — Brinks Gilson & Lione

(57) ABSTRACT

The present invention relates to aqueous suspension concentrate formulation for plant protection comprising:

2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide in the form of its crystalline anhydrate;

at least one non-ionic surfactant selected from polyoxyethylene-polyoxy-$C_3$-$C_4$-alkylene block copolymers;

at least one anionic surfactant comprising at least one arylsulfonate group; and water;

wherein the pH value of the formulation is in the range of 3 to 7.

16 Claims, No Drawings

AQUEOUS SUSPENSION CONCENTRATE FORMULATIONS CONTAINING SAFLUFENACIL

This application is a National Stage application of International Application No. PCT/EP2010/062473, filed Aug. 26, 2010, which claims the benefit of U.S. Provisional Application No. 61/237,406, filed Aug. 27, 2009, the entire contents of which are hereby incorporated herein by reference.

The present invention relates to new aqueous suspension concentrate formulations of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide, herein after also referred to with its common name "saflufenacil". The invention also relates to the use of the formulations for controlling undesired vegetation and to corresponding methods.

Saflufenacil is a herbicidal active substance having the following formula I,

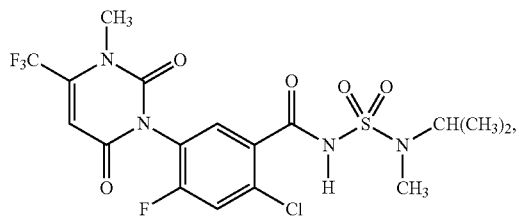

which has been disclosed in WO 01/083459. Further processes for its preparation are described in WO 03/097589, WO 05/054208, WO 06/097589 and WO 06/125746. A crystalline and essentially solvent-free form of saflufenacil, herein after also referred to as the crystalline anhydrate form, is disclosed in WO 08/043,835.

For the purpose of application by the end user, herbicide compounds may be formulated in solid forms, such as wettable powders and granules, as well as in liquid forms, such as emulsifiable concentrates (ECs) or suspension concentrates (SCs). The latter ones can be diluted with water for use in the field and thus usually provide an easy-to-handle way of application. However, like many active ingredients that are used as herbicides, salfufenacil is only sparingly soluble in water and mixtures of water with water-miscible solvents such as $C_1$-$C_4$-alkanols or $C_2$-$C_4$-alkandiols and -triols. Nonetheless, application of herbicides in the form of dilute aqueous suspension concentrates, i.e. in the form of spray liquors, is favorable for ease of application.

Suspension concentrates (SC's) are formulations, wherein the active ingredient is present in the form of finely divided solid particles, which are suspended (dispersed) in a liquid dispersing medium such as water or polyhydric alcohols, wherein the active ingredient is insoluble or only sparingly soluble (less than 2000 ppm). Suspension concentrates usually contain surface-active compounds (surfactants), such as dispersants and wetting agents for stabilizing the active ingredient particles in the dispersing medium.

Despite the aforementioned advantages associated with the usage of SCs, there are a number of problems known to the skilled person which are sometimes encountered with SCs as a result of settling during prolonged storage or storage at elevated temperatures, the resistance of settled particles to re-suspension and the formation of crystalline material upon storage. As a consequence, the formulations may be difficult to handle and the bioefficacy may be inconsistent.

When trying to formulate saflufenacil one faces several problems. Saflufenacil carries a N-amino-sulfonylcarboxamide side-chain which might undergo hydrolysis at basic pH values. Apart from that, saflufenacil is capable of existing in different crystalline and non-crystalline modifications, namely amorphous forms, crystalline hydrates and a crystalline anhydrate, which may undergo uncontrolled interconversion. This interconversion in turn may lead to coarsening of the saflufenacil particles, in particular when formulated as suspension concentrate. These factors might result in a reduced chemical and physical stability of the formulations, an effect that is particularly pronounced when the formulations are stored over prolonged periods of time and/or at elevated temperatures. Said factors may also lead to poor dilution properties as the coarse saflufenacil particles are prone to separate from the diluted formulation.

Up to now, saflufenacil is available only in the form of wettable granule formulations and as emulsion concentrate with low a.i. loading. An aqueous suspension concentrate formulation with prolonged storage stability even at elevated temperatures and with good dilution properties has not yet been reported.

Therefore, it is an object of the present invention to provide an aqueous suspension concentrate formulation of saflufenacil that shows both high physical and chemical stability over prolonged storage periods while maintaining its biological efficacy. It should also be compatible with tank-mix partners which are commonly combined with saflufenacil. Upon dilution with water, the formulation should give a stable aqueous composition of saflufenacil without forming coarse material or a supernatant liquid.

Surprisingly this object is achieved by formulating saflufenacil in the form of its crystalline anhydrate together with certain non-ionic and certain anionic surfactant as an aqueous suspension concentrate having a pH value in the range of from 3 to 7.

Therefore, the present invention relates to an aqueous suspension concentrate formulation for plant protection, comprising the components:
a) saflufenacil in the form of its crystalline anhydrate;
b) at least one non-ionic surfactant selected from ethylene oxide/$C_3$-$C_4$-alkylene oxide block copolymers;
c) at least one anionic surfactant comprising at least one arylsulfonate group; and
d) water;
wherein the pH value of the formulation is in the range of 2 to 7, in particular in the range from 4 to 6 and especially in the range from 4.5 to 5.5.

A pH value within the stated range in coaction with the specific surfactants unexpectedly imparts a good to excellent overall stability to the formulation of the invention. That is, over prolonged storage periods, the highly active but degradation-prone saflufenacil remains intact in the form of its anhydrate modification and the formulation remains homogenous while affording stable dispersions on dilution. Without being bound to theory it is believed that the neutral to slightly acidic pH value on one hand stabilizes the anhydrate form while still allowing the anionic surfactant to be fully effective. Thus, by employing the combination of surfactants and adjusting the pH value in the range given above it is surprisingly possible to balance the chemical stability of the anhydrate form with the physical stability of the formulation.

In conclusion, the aqueous suspension concentrate formulations of the present invention exhibit good physical and chemical stability over prolonged storage times. Thus neither significant phase separation phenomena such as agglomeration of saflufenacil occur nor does the saflufenacil anhydrate degrade to a noticeable extent or change into a different modification.

As used herein, $C_3$-$C_4$-alkylene oxide refers to an epoxide ring wherein the carbon atoms of the epoxide ring is substituted with one or two methyl groups or with one ethyl group. Specifically, $C_3$-$C_4$-alkylene oxide refers to propylene oxide, 1,2-butylene oxide, cis- or trans-2,3-butylene oxide and/or isobutylene oxide.

As used herein, $C_2$-$C_5$ alkanediol refers to a cyclic, straight-chained or branched alkanols which have from 2 to 5 carbon atoms and which carry two OH moieties, examples including ethylene glycol, 1,2-propanediol, 1,3-propanediol, 1,4 butanediol and 2,4-pentanol.

As used herein, $C_3$-$C_8$ alkanediol refers to a cyclic, straight-chained or branched alkanols which have from 3 to 8 carbon atoms and which carry three OH moieties, examples including glycerol, 1,2,3-butanetriol, 1,2,4-butanetriol, 1,3,5-cyclohexanetriol, 2,4,6-heptanetriol and 3-methyl-pentane-1,2,4-triol.

As stated before, the crystalline anhydrate form of saflufenacil employed in the formulation of the invention refers to the saflufenacil modification that has been disclosed in WO 08/043,835. Accordingly, the crystalline anhydrate form is an essentially solvent-free crystalline form of saflufenacil (compound of formula I). In this connection the term "essentially solvent-free" means that the crystalline anhydrate form comprises no detectable amounts of solvents incorporated into the crystal lattice, i.e. the amount of solvent in the crystal lattice is less than 10 mol %, in particular not more than 5 mol %, based on saflufenacil.

The crystalline anhydrate form can be identified by means of X-ray powder diffractometry on the basis of its diffraction diagram. Thus, an X-ray powder diffractogram recorded at 25° C. using Cu—Kα radiation (1.54178 Å) shows at least 2, as a rule at least 4, frequently at least 6, in particular at least 8 and specifically all of the reflexes detailed in Table 1 hereinbelow as 2θ values, or as interplanar spacings d:

TABLE 1

| 2θ | d [Å] |
|---|---|
| 6.3 ± 0.2° | 14.92 ± 0.3 |
| 9.4 ± 0.2° | 9.37 ± 0.2 |
| 10.9 ± 0.2° | 8.15 ± 0.1 |
| 11.9 ± 0.2° | 7.45 ± 0.05 |
| 12.6 ± 0.2° | 7.02 ± 0.05 |
| 15.0 ± 0.2° | 5.90 ± 0.05 |
| 15.8 ± 0.2° | 5.62 ± 0.04 |
| 17.1 ± 0.2° | 5.19 ± 0.03 |
| 20.0 ± 0.2° | 4.44 ± 0.02 |
| 20.4 ± 0.2° | 4.36 ± 0.02 |
| 24.7 ± 0.2° | 3.61 ± 0.02 |
| 25.2 ± 0.2° | 3.53 ± 0.02 |
| 26.2 ± 0.2° | 3.40 ± 0.02 |

Studies on monocrystals of the anhydrate form at −170° C. demonstrate that the underlying crystal structure is monoclinic. The unit cell has the space group P2(1)/c. The characteristic data of the crystal structure of the anhydrate form are compiled in Table 2.

TABLE 2

Crystallographic characteristics of the crystalline anhydrate form (measured at −170° C.)

| Parameter | Form II |
|---|---|
| class | monoclinic |
| space group | P2(1)/c |
| a | 9.377(5) Å |
| b | 7.698(4) Å |
| c | 28.12(2) Å |
| α | 90° |
| β | 96.37(3)° |
| γ | 90° |
| volume | 2017.1(17) Å 3 |
| Z | 4 |
| density (calculated) | 1.649 mg/m$^3$ |
| R1; wR2 | 0.057; 0.149 |
| wavelength | 1.54178 Å | a, b, c = unit cell length
α, β, γ = unit cell angle
Z = number of molecules in the unit cell Besides X-ray powder diffractometry and the crystallographic analysis, differential scanning calorimetry (DSC) can also be employed for identifying the anhydrate form. Thus, the anhydrate form shows a thermogram with a characteristic melting peak in the range between 170 and 200° C. The peak maximum is typically in the range of approximately 180° C. to 190° C. The melting points indicated herein refer to data determined by means of differential scanning calorimetry (DSC, crucible material aluminum, heating rate 5 K/min).

The crystalline anhydrate form of saflufenacil may be prepared by controlled crystallization from a solution of saflufenacil in an organic solvent which is essentially free from water as described in WO 08/043,835.

The invention relates in particular to formulations for plant protection in the form of an aqueous suspension concentrate (SC). Such suspension concentrates comprise the crystalline anhydrate modification of saflufenacil, herein also referred to as saflufenacil anhydrate, in a finely divided particulate form, where the particles of the saflufenacil anhydrate are suspended in an aqueous phase. The size of the saflufenacil anhydrate particles, i.e. their diameter, will in general not exceed 20 μm, preferably not exceed 10 μm and in particular not exceed 5 μm. The particle size given is the so called $D_{90}$-value, which has to be understood as the value that is not exceeded by the diameters of at least 90% by weight of the particles. Preferably the active substance particles have an average particle diameter, herein also termed $D_{50}$-value, ranging from 0.5 to 20 μm, in particular from 1 to 5 μm. The $D_{50}$-value is defined as the value that is above the diameters of 50% by weight of the particles and below the diameters of 50% by weight of the particles. Advantageously, at least 40% by weight, preferably at least 60% by weight and in particular at least 80% by weight of the particles in the SC formulations according to the invention have sizes, i.e. diameters, of below 3 μm. The particle size of the active substance particles (i.e. the diameters) can be determined by conventional methods such as light-scattering.

The particles of saflufenacil anhydrate contained in the SC formulation of the invention are solid a.i. particles, i.e. the particles mainly contain the pure saflufenacil anhydrate. The purity of the saflufenacil anhydrate is usually at least 90% by weight, preferably at least 95% and in particular at least 97% by weight, i.e. the saflufenacil anhydrate makes up at least 90%, preferably at least 95% and in particular at least 97% by weight of the insoluble material present in the composition.

The concentration of saflufenacil anhydrate in the formulation of the invention may usually be from 5 to 60% by weight, in particular from 10 to 55% by weight, more preferably from 15 to 40% by weight, based on the total weight of the formulation.

According to the invention the saflufenacil anhydrate is insoluble or only sparingly soluble in the aqueous phase of the formulations at the above pH values, i.e. at 25° C./1013 mbar the solubility of the saflufenacil anhydrate in the aqueous phase of the formulation is not more than 1% by weight, in particular not more than 0.1% by weight and specifically not more than 0.01% by weight.

In the context of this invention the term "aqueous phase" stands for the liquid component of the formulation comprising an aqueous solvent and compounds solved therein. The aqueous solvent of the present invention is either water or a mixture thereof with a water-miscible organic solvent, which is selected from $C_2$-$C_5$-alkanediols and $C_3$-$C_8$-alkanetriols, preferably from the group consisting of ethylene glycol, 1,2-propanediol, 1,3-propanediol, glycerol and 1,4-butanediol, and more preferably from 1,2-propanediol and 1,3-propanediol. According to a particular preferred embodiment of the invention the organic solvent is 1,2-propanediol.

The amount of aqueous solvent in the formulation of the invention may usually be from 30 to 95% by weight or 30 to 94.98% by weight, in particular from 35 to 90% by weight or 35 to 89.8% by weight, more preferably from 40 to 84.8% by weight or 40 to 83.5% by weight, based on the total weight of the formulation.

In a first preferred embodiment of the invention the aqueous solvent consists mainly of water, i.e. water makes up at least 99% by weight of the total amount of solvent present in the formulation. In a more preferred embodiment of the invention the aqueous solvent is a mixture of the aforementioned water-miscible organic solvent and water. In the latter case, the weight ratio of water to water-miscible organic solvent in the aqueous solvent preferably is in the range of from 99:1 to 1:1; more preferably in the range of from 84:1 to 2:1; and most preferably in the range of from 30:1 to 5:1. Expressed differently the amount of organic solvent may preferably be from 0.5 to 45% by weight, more preferably from 1 to 20% by weight, and most preferably from 2 to 10% by weight, based on the total weight of the formulation.

The at least one anionic surfactant c) of the formulation of the invention comprises at least one arylsulfonic acid group and is preferably selected from:

c1) aryl- and $C_1$-$C_{16}$-alkylarylsulfonates such as naphthylsulfonate, mono-, di- and tri-$C_1$-$C_{16}$-alkylnaphthylsulfonates such as dibutylnaphtylsulfonate, dodecyldiphenylether sulfonate, mono-, di- and tri-$C_1$-$C_{16}$-alkylphenylsulfonates such as cumylsulfonate, octylbenzene sulfonate, nonylbenzenesulfonate, dodecylbenzene sulfonate and tridecylbenzene sulfonate; and c2) polymeric anionic surfactants having $SO_3^-$ groups bound to an aromatic moiety such as a phenyl or a naphthyl ring, e.g. condensates of arylsulfonic acid with formaldehyde and optionally in addition with urea, such as naphthalene sulfonic acid formaldehyde condensates, phenol sulfonic acid formaldehyde condensates, cresol sulfonic acid formaldehyde condensates, ligninsulfonates, etc; and the salts thereof The sulfonate groups of the surfactants included in the formulations of the invention may be partially or fully neutralized. Suitable counter ions are alkali metal ions such as sodium or potassium, earth alkaline metal ions such as magnesium or calcium as well as ammonium.

In the group of surfactants c1) preference is given to mono- or di-$C_4$-$C_8$-alkylnaphthaline sulfonic acid and mono- or di-$C_4$-$C_{16}$-alkylbenzesulfonic acid and the salts thereof, in particular alkaline metal salts, such as the sodium or potassium salt, and the earth alkaline metal salts, such as the calcium salts thereof.

The arylsulfonic acids incorporated into the formaldehyde condensates of the surfactant group c2) may be e.g. phenol sulfonic acids or naphthalene sulfonic acids which are unsubstituted or substituted by one or more, e.g. 1, 2, 3 or 4 $C_1$-$C_{20}$ alkyl groups. In a preferred embodiment, the surfactant c2) is an alkaline metal salt or earth alkaline metal salt of a reaction product (condensate) of phenol sulfonic acid and formaldehyde; particularly suitable example are Tamol® DN (BASF), Tamol® PP (BASF) and Wettol® D1 (BASF).

The total amount of anionic surfactant is preferably in the range from 0.01 to 20% by weight, in particular from 0.1 to 10% by weight, more preferably from 0.5 to 3% by weight, based on the total weight of the formulation.

The at least one non-ionic surfactant b) of the formulation of the invention is a polyoxyethylene-polyoxy-$C_3$-$C_4$-alkylene block copolymer selected form non-ionic block copolymers comprising at least one poly(ethylene oxide) moiety PEO and at least one polyether moiety PAO derived from $C_3$-$C_4$-alkylene oxides, in particular selected from polyoxyethylene-polyoxypropylene-block copolymers.

The at least one PAO moiety of the non-ionic block copolymer b) usually comprises at least 3, preferably at least 5, in particular 10 to 100 repeating units (number average) which are derived from $C_3$-$C_4$ alkylene oxides, such as propylene oxide, 1,2-butylene oxide, cis- or trans-2,3-butylene oxide or isobutylene oxide. Preferably, the PAO moieties comprise at least 50% by weight, and more preferably at least 80% by weight of repeating units derived from propylene oxide. The at least one PEO moiety of the non-ionic block copolymer b) usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:10 to 2:1, more preferably from 2:8 to 7:3 and in particular from 3:7 to 6:4. Those surfactants b) are preferred which have a number average molecular weight $M_N$ ranging from more than 1200 to 100000 Dalton, preferably from 2000 to 60000 Dalton, more preferably from 2500 to 50000 Dalton and in particular from 3000 to 20000 Dalton. In general, the PEO moieties and the PAO moieties make up at least 80% by weight, and preferably at least 90% by weight, e.g. 90 to 99.5% by weight, of the non-ionic block copolymer surfactants b). Suitable surfactants b) are described e.g. in WO 06/002984, in particular those having the formulae P1 to P5 given therein.

The non-ionic block copolymer surfactants b) described herein are commercially available e.g. under the trade names Pluronic®, such as Pluronic® PE 3100, PE 3500, PE 4300, PE 6100, PE 61200, PE 6200, PE 6400, PE 6800, PE 8100, PE 9200, PE 9400, PE 10100, PE 10400, PE 10500, RPE 1720, RPE 1740, RPE 2520, RPE 2525 and RPE 3110 (BASF SE). Among these a particularly suitable example is Pluronic® PE 10500, and the like.

The total amount of non-ionic surfactant is preferably in the range from 0.01 to 20% by weight, in particular from 0.1 to 10% by weight, more preferably from 1 to 5% by weight or from 1 to 4% by weight, based on the total weight of the formulation.

According to a preferred embodiment of the present invention the formulation of the invention comprises:

a) from 10 to 50% by weight, frequently from 15 to 40% by weight, preferably from 25 to 35% by weight, based on the total weight of the composition, of saflufenacil in the form of its crystalline anhydrate;
b) from 0.1 to 10% by weight, preferably from 1 to 5% by weight or from 1 to 4% by weight, based on the total weight of the composition, of at least one non-ionic surfactant selected from polyoxyethylene-polyoxy-$C_3$-$C_4$-alkylene block copolymers;
c) from 0.1 to 10% by weight, preferably from 0.5 to 3% by weight, based on the total weight of the composition, of at least one anionic surfactant comprising at least one arylsulfonic acid group; and
d) from 30 to 89.8% by weight, frequently from 40 to 84.8% by weight, preferably from 52 to 74.5% by weight or from 52 to 73.5% by weight, based on the total weight of the composition, of an aqueous solvent.

The compositions according to the invention may also comprise customary adjuvants, such as viscosity-modifying additives (thickeners), antifoam agents, preservatives, buffers, inorganic dispersants, etc, which are usually employed in aqueous formulations of herbicides. Such adjuvants may be incorporated into the formulations of the invention either before or after step (ii) of the preparation process described herein has been carried out. They may also be incorporated after step (iii) of the preparation process described herein has been carried out. Preferably these adjuvants are added after completion of step (ii) and before step (iii) of the preparation process. The amount of additives will generally not exceed 10% by weight, in particular 5% by weight of the total weight of the composition.

Suitable inorganic dispersants, also termed anticaking agents, for preventing agglutination of the a.i. particles, are silica (such as, for example Sipernat® 22 from Degussa), alumina, calcium carbonate and the like. In the context of the present invention silica is a preferred inorganic dispersant. The concentration of inorganic dispersants in the final suspension concentrates will generally not exceed 10% by weight, based on the total weight of the final suspension concentrate, and is preferably in the range from 0.01 to 3% by weight, in particular from 0.02 to 1.5% by weight and especially from 0.1 to 1% by weight, based on the total weight of the final suspension concentrate.

Suitable thickeners are compounds which affect the flow behavior of the suspension concentrate and may assist in stabilizing the suspension concentrate against caking. Mention may be made, in this connection, for example, of commercial thickeners based on polysaccharides, such as methylcellulose, carboxymethylcellulose, hydroxypropylcellulose (Klucel® grades), Xanthan Gum (commercially available e.g. as Kelzan® grades from Kelco or Rhodopol® grades from Rhodia), synthetic polymers such as acrylic acid polymers (Carbopol® grades), polyvinyl alcohol (e.g. Mowiol® and Poval® grades from Kuraray) or polyvinyl pyrrolones, silicic acid or phyllosilicates such as montmorillonite and bentonites, which may be hydrophobized, (commercially available as Attaclay® grades and Attaflow® grades from BASF SE; or as Veegum® grades and Van Gel® grades from R.T. Vanderbilt). In the context of the present invention Xanthan Gum is a preferred thickener. The concentration of thickeners in the final suspension concentrates will generally not exceed 2% by weight, based on the total weight of the final suspension concentrate, and is preferably in the range from 0.01 to 2% by weight, in particular from 0.02 to 1.5% by weight and especially from 0.1 to 1% by weight, based on the total weight of the final suspension concentrate.

Antifoam agents suitable for the formulations according to the invention are, for example, silicone emulsions (such as, for example, Silicone SRE-PFL from Wacker or Rhodorsil® from Bluestar Silicones), long-chain alcohols, fatty acids, organofluorine compounds and mixtures thereof.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. Commercially available preservatives that are based on isothiazolinones are for example marketed under the trademarks Proxel® (Arch Chemical), Acticide® MBS (Thor Chemie) and Kathon® MK (Rohm & Haas).

If appropriate, the aqueous SC formulations according to the invention may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

In addition, the aqueous SC formulations according to the invention can be formulated with conventional binders, for example aqueous polymer dispersions, water-soluble resins, for example water-soluble alkyd resins, or waxes.

The formulations of the present invention can be prepared by a process comprising the following steps:
(i) providing a suspension of saflufenacil anhydrate in a mixture of the aqueous solvent and the surfactants;
(ii) reducing the particle size of the saflufenacil anhydrate present in the suspension of step (i), preferably to the size specified above;
(iii) optionally adjusting the pH value within the range of 2 to 7, if necessary.

In order to prepare the suspension of step (i), saflufenacil anhydrate, the aqueous solvent and the surfactant are mixed in any conventional mixing device which is capable of providing sufficient shear to form the desired suspension. Suitable mixing devices include in particular high shear mixers, such as Ultra-Turrax apparatus, static mixers, e.g. systems having mixing nozzles, agitator bead mills, colloid mills, cone mills and other homogenizers.

In general, the sequence in which the individual components are combined is not critical. However, it may be advantageous to carry step (i) out by firstly mixing the solvent and the surfactant until a homogenous mixture is obtained, and then adding the saflufenacil anhydrate with shear to said homogenous mixture. Thus, step (i) yields a mixture including the components a), b) c), and d), wherein saflufencacil (component a)) is present in the form of solid particles which are dispersed in the homogeneous phase formed by the solvent and the surfactant.

The mixture obtained from step (i), i.e. in the form of a suspension, is subjected in step (ii) to suitable means for reducing the particle size of the saflufenacil anhydrate particles present in the mixture typically to below 20 μm, preferably to below 10 μm and in particular to below 5 μm ($D_{90}$-value). The step (ii) may be carried out by any physical attrition method, such as grinding, crushing or milling, in particular by wet grinding or wet milling, including e.g. bead milling, hammer milling, jet milling, air classifying milling, pin milling, cryogenic grinding processes and the like.

Steps (i) and (ii) are usually performed subsequently. However it is also possible to perform these steps together.

If necessary, i.e. if the pH of the aqueous suspension obtained in steps (i) or (ii) is outside the range according to the invention, the pH of the suspension obtained in steps (i) or (ii)

will be adjusted in step (iii) to the claimed range. The adjustment of the pH value of the formulation in step (iii) can be effected in manner known per se using methods for pH measurement well known in the art, in particular those employing a pH electrode. The pH is usually adjusted by adding an acid or a base to the aqueous suspension obtained in steps (i) or (ii). However, a suitable buffer providing a pH in the desired range may also be added. Preferred acids for this purpose are dilute mineral acids such as HCl, $HNO_3$, $H_2SO_4$ or $H_3PO_4$, or dilute organic acids such as acetic acid. Preferred bases in this regard are dilute alkali metal hydroxides such as NaOH or KOH, and alkaline earth metal hydroxides such as magnesium hydroxide or calcium hydroxide. Preferably, the pH is adjusted with dilute acetic acid. By this means the pH is brought to a value in the range of from 2 to 7, in particular in the range of from 4 to 6 and especially preferably in the range of from 4.5 to 5.5.

Step (iii) is usually performed subsequent to steps (i) and (ii) so that its completion affords the final SC formulation according to the present invention. Alternatively, step (iii), if required, may also be performed prior to step (ii), either during or following step (i).

The invention also relates to uses of the aqueous SC formulation of the invention for protecting crop plants and to methods of controlling undesired vegetation, which comprise applying the formulations, in diluted or undiluted form, to plants, their environment and/or seeds.

The herbicidal formulations of the invention affect a very good control of vegetation in non-crop areas, especially at high application rates. In crops such as soybean, cotton, oilseed rape, flax, lentils, rice, sugar beet, sunflower, tobacco and cereals, such as, for example maize or wheat, they are active against broad-leaved weeds and grass weeds without inflicting substantial damage to the crop plants. This effect is particularly observed at low application rates.

Depending on the application method in question, the formulations of the invention can additionally be employed in a further number of crop plants to remove undesired plants. Crops which are suitable are, for example, the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pisum sativum, Prunus armeniaca, Prunus avium, Prunus cerasus, Prunus dulcis, Prunus domesticua, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays*.

In addition, the formulations of the invention can also be used in crops which tolerate the effect of herbicides as the result of breeding, including genetic engineering methods.

Furthermore, the formulations of the invention can also be used in crops which tolerate attack by insects or fungi as the result of breeding, including genetic engineering methods.

Moreover, it has been found that the formulations of the invention are also suitable for the defoliation and desiccation of plant parts, for which crops plants such as cotton, potato, oilseed rape, sunflower, soybean or field beans, in particular cotton, are suitable.

As desiccants, the formulations of the invention are particularly suitable for desiccating the aerial parts of crop plants such as potato, oilseed rape, sunflower and soybean. This makes possible the fully mechanical harvesting of these important crop plants. Also of economic interest is to facilitate harvesting, which is made possible by concentrating within a certain period of time the dehiscence, or reduction of adhesion to the tree, in citrus fruit, olives or other species and varieties of pome fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval within which the individual cotton plants mature leads to an increased fiber quality after harvesting.

Moreover, it has been found that the formulations of the invention are also suitable for the control of conifers, in particular of conifer seedlings which grow naturally, and specifically for the control of pine seedlings which grow naturally.

In general, the aqueous SC formulations described herein are useful for combating undesired vegetation. For this purpose, the formulations may be applied as such or are preferably applied after dilution with water. Preferably, for various purposes of end user application, a so-called aqueous spray-liquor is prepared by diluting the aqueous SC formulation of the present invention with water, e.g. tap water. The spray-liquors may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and nonphytotoxic oils or oil concentrates. As a rule, these constituents are added to the spray mixture before, during or after dilution of the formulations according to the invention.

The formulations of the invention can be applied by the pre-emergence or the post-emergence method. If the saflufenacil is less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Depending on the aim of the control measures, the season, the target plants and the growth stage, the formulations of the invention are applied to such a degree that the application rates of saflufenacil are from 0.001 to 3.0, preferably from 0.01 to 1.0 kg/ha active substance (a.s.).

To widen the spectrum of action and to obtain synergistic effects, the aqueous SC formulations of the invention can be mixed with a large number of representatives of other groups of herbicidal or growth-regulatory active substances and applied together with these.

Examples of suitable mixing partners are 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothia-diazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetero-aryloxyphenoxypropionic acid esters, phenylacetic acid and its derivatives, 2-phenyl-propionic acid and its derivatives, pyrazoles, phenylpyrazoles, pyridazines, pyridine-carboxylic acid and its derivatives, pyrimidyl ethers, sulfonamides, sulfonylureas, triazines, triazinones, triazolinones, triazolecarboxamides and uracils.

It is of also possible to use the aqueous suspension concentrate formulations of the present invention as a tank-mix partner with other formulations. Thus, the formulations of the invention can be mixed and applied together with a large number of different pesticide compound formulations, for example those that include active ingredients or adjuvants, such as atrazine, glyphosate, glufosinate, S-metolachlor, 2,4-D ester, isoxaflutole, diflufenzopyr, dicamba, mesotrione, dimethenamid-P, pendimethalin, imazethapyr, paraffin oils, polyol fatty acid esters, polyethoxylated polyol fatty acid esters, ethoxylated alkyl aryl phosphates, methylated seed oils, emulsifiers, ammonium sulfate or mixtures thereof.

Moreover, it may be useful to apply the saflufenacil-containing formulations of the invention, separately or in combination with other herbicides, jointly as a mixture with yet further plant protection agents, for example with agents for controlling pests or phytopathogenic fungi or bacteria. Also of interest is the miscibility with mineral salt solutions which are employed for alleviating nutritional and trace element deficiencies. Nonphytotoxic oils and oil concentrates may also be added.

The following examples are intended to further illustrate the present invention without limiting its scope in any way.

I. Analytics:

Particle sizes were determined by dynamic light scattering with a Malvern Mastersizer 2000 system at 23° C.

Viscosities were measured in analogy to DIN EN ISO 255 with a Brookfield DV-E Viscometer, spindle 1 of the RV spindle set at 50 m$^{-1}$. Alternatively or in addition dynamic viscosities were determined in analogy to OECD Test Guideline 114 ("Viscosity of Liquids").

The pH values of the formulations were determined according to the test method of the Collaborative International Pesticides Analytical Council CIPAC MT 75.3. Measurements were carried out with 1% (v/v) solutions of the aqueous suspension concentrate formulations in "water D" as defined by CIPAC.

II. Ingredients:

Surfactant 1: Sodium salt of a phenolsulfonic acid-formaldehyde polycondensate—Tamol® DN (BASF SE)

Surfactant 2: Blockcopolymer of ethylene oxide and propylene oxide, $M_N$ 6500, EO/PO ratio 50:50—Pluronic® PE 10500 (BASF SE)

Antifoam agent: Polydimethylsiloxane emulsion—Silicone SRE-PFL (Wacker)

Inorganic dispersant: Silica—Sipernat® 22 (Evonik)

Thickener: Xanthan Gum—Kelzan® (Kelco)

Preservative: 1,2-benzisothiazolin-3-one—Acticide® MBS (Thor Chemie)

III. Preparation of the Compositions of the Invention:

EXAMPLE 1

Surfactant 1 (20 g) and surfactant 2 (30 g) were dissolved in a mixture of water (673 g) and 1,2-propylene glycol (70 g), and agitation was continued until a homogenous phase was obtained. Then saflufenacil anhydrate (342 g) was added and dispersed using a high shear mixer. The thus obtained slurry was then passed through a bead mill (Eiger Mini 50) using 0.8 mm beads with a bead loading of 90% until a particle size of below 3 µm for at least 80% by weight of the saflufenacil was achieved. Then the antifoam agent (5 g), the inorganic dispersant (5 g), the thickener (3 g) and the preservative (2 g) were added and the resulting mixture was homogenized. Finally the pH value of the obtained composition was adjusted to pH 5 with diluted aqueous acetic acid (0.2 g/L).

IV. Chemical Stability

Samples of the aqueous SC formulation obtained according to Example 1 were stored at 20° C., 30° C., 40° C. and 50° C., respectively, for a period of 6 month. The chemical stability was then assessed by determining the remaining proportion of intact saflufenacil anhydrate in the samples using HPLC. The results revealed that the saflufenacil anhydrate did not noticeably decompose or change into a different modification. Thus, under the aforementioned storage conditions the saflufencacil anhydrate is virtually stable.

V. Physical Stability

1. Stability after Prolonged Storage at Elevated Temperatures

The stabilities of stored formulations were evaluated on the basis of the quality of the dispersions obtained therefrom by dilution.

Initially a sample of an aqueous SC formulation that was freshly prepared according to Example 1 was diluted with water (2 g of the formulation with 98 g water) in analogy to the preparation of a spray liquor. A stable white dispersion without sediment was obtained.

Samples of the formulation were then stored at 20° C., 30° C., 40° C. and 50° C., respectively, for a period of 6 month and afterwards diluted with water as described above. The resulting dispersions were examined for their physical properties after storage for 2 hours at 20° C. In all cases no or only minor sedimentation accounting for less than 2% of the total weight of the saflufenacil was observed.

2. Stability after Freeze-Thaw Cycles

The stabilities of freeze-thaw-cycled formulations were evaluated based on of the quality of the dispersions obtained therefrom by dilution and based on their appearances, viscosities and particle size distributions.

Samples of the formulation prepared according to Example 1 were subjected to 28 cycles of freezing and thawing either between −10° C. and +10° C. or between −5° C. and +30° C. Afterwards no residue, phase separation or crystallization was observed in any of the samples. Also, the viscosities of all samples as well as their particle size distributions remained unchanged. In addition, the freeze-thaw-cycled samples were diluted with water as described above. The resulting dispersions revealed no or only minor sedimentation of less than 2% of the total weight of the saflufenacil after storage for 2 hours at 20° C.

In conclusion, the overall stability at low to medium temperatures of the formulation of Example 1 is very good.

V. Herbicidal Activity

The effect of the aqueous SC formulations according to the invention on the growth of undesirable plants was demonstrated by the following pre- and post-emergence treatment greenhouse experiments.

In the case of pre-emergence applications the spray liquor was applied to the surface of the soil patch in which the seeds or the seedlings of a test plant were present. In the case of post-emergence application the test plants were first grown to a height of 3 to 20 cm, depending on the plant habit, and only then treated with the spray liquor. In both cases the spray liquor was prepared by diluting the formulation according to Example 1 with water to a level customary for saflufenacil. Both, the soils and test plants were sprayed using finely distributing nozzles to the extent that in all cases application rates of 12.5 g saflufenacil per hectare were reached.

The test period extended over 19 (post-emergence application) or 20 (pre-emergence application) days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The plants used in the greenhouse experiments belonged to the following species:

| Scientific Name | Code | Common Name |
|---|---|---|
| *Abutilon theoprasti* | ABUTH | velvetleaf |
| *Amaranthus retroflexus* | AMARE | redroot pigweed |
| *Ambrosia artemisiifolia* | AMBEL | common ragweed |
| *Bidens pilosa* | BIDPI | broom stick |
| *Capsella bursa-pastoris* | CAPBP | shepherd's-purse |
| *Chenopodium album* | CHEAL | white goosefoot |
| *Commelina benghalensis* | COMBE | benghal dayflower |
| *Convolvulus arvensis* | CONAR | field bindweed |
| *Conyza canadensis* | ERICA | horseweed |
| *Panicum dichotomiflorum* | PANDI | smooth witchgrass |
| *Ipomoea purpurea* (L.) Roth | PHBPU | common morningglory |
| *Fallopia convolvulus* | POLCO | wild buckwheat |
| *Solanum nigrum* | SOLNI | black nightshade |
| *Thlaspi arvense* | THLAR | field penny-cress |
| *Veronica persica* | VERPE | persian speedwell |

Table 3 relates to the herbicidal activity of saflufenacil assessed 19 or 20 days after treatment (DAT).

TABLE 3

Application in pre- and post-emergence of the formulation according to Example 1 in diluted form

| Weed | DAT | application mode | application rate of saflufenacil [g/ha] | observed herbicidal activity [%] |
|---|---|---|---|---|
| ABUTH | 20 | pre-emergence | 12.5 | 100 |
| AMARE | 20 | pre-emergence | 12.5 | 100 |
| AMBEL | 20 | pre-emergence | 12.5 | 100 |
| BIDPI | 20 | pre-emergence | 12.5 | 95 |
| CAPBP | 20 | pre-emergence | 12.5 | 100 |
| CHEAL | 20 | pre-emergence | 12.5 | 100 |
| COMBE | 20 | pre-emergence | 12.5 | 100 |
| CONAR | 20 | pre-emergence | 12.5 | 100 |
| ERICA | 20 | pre-emergence | 12.5 | 100 |
| PANDI | 20 | pre-emergence | 12.5 | 100 |
| PHBPU | 20 | pre-emergence | 12.5 | 100 |
| POLCO | 20 | pre-emergence | 12.5 | 100 |
| SOLNI | 20 | pre-emergence | 12.5 | 100 |
| THLAR | 20 | pre-emergence | 12.5 | 100 |
| VERPE | 20 | pre-emergence | 12.5 | 100 |
| ABUTH | 19 | post-emergence | 12.5 | 100 |
| AMBEL | 19 | post-emergence | 12.5 | 100 |
| BIDPI | 19 | post-emergence | 12.5 | 100 |
| CONAR | 19 | post-emergence | 12.5 | 100 |
| ERICA | 19 | post-emergence | 12.5 | 100 |
| PHBPU | 19 | post-emergence | 12.5 | 100 |
| SOLNI | 19 | post-emergence | 12.5 | 100 |

As can be seen from table 3 the formulation of the invention shows high herbicidal activity in pre- as well as in post-emergence applications against a variety of weed targets already 20 respectively 19 days after treatment.

VI. Tank Mix Compatibility

The compatibility of the SC formulation of Example 1 with the tank-mix partners listed in the table 4 was tested in a laboratory application test. Compatibility was approved for all the tank-mix partners listed in table 4.

TABLE 4

Tested and approved tank mix partners

| Active ingridient | Formulation type |
|---|---|
| Atrazine (e.g. Atrazine 4L from Syngenta) | SC |
| Atrazine and S-metolachlor (e.g. Bicep II Magnum from Syngenta) | SC |
| 2,4-D ester such as 2,4-D-butotyl | EC |
| Isoxaflutole (e.g. Balance Pro from Bayer) | SC |
| Diflufenzopyr and dicamba (e.g. Distinct 70 WG from BASF) | WG |
| S-Metolachlor (e.g. Dual II Magnum from Syngenta) | EC |
| Atrazine, S-metolachlor and mesotrione (e.g. Lumax from Syngenta) | SC |
| Dimethenamid-P (e.g. Outlook from BASF) | EC |
| Pendimethalin (e.g. Prowl H2O from BASF) | CS |
| Pendimethalin (e.g. Prowl 3.3 from BASF) | EC |
| Imazethapyr ammonium salt (e.g. Pursuit from BASF) | WG |
| Blend of paraffin oils, polyol fatty acid esters, polyethoxylated esters thereof and ethoxylated alkyl aryl phosphate (Penetrator Plus from Helena Chemical) | (adjuvant) |
| Methylated seed oil and emulsifiers, Agsco (Sunit II, Agsco) | (adjuvant) |
| Ammonium sulfate | (adjuvant) |

SC: suspension concentrate
WG: wettable granules
EC: emulsifiable concentrate
CS: capsule suspension

The invention claimed is:

1. Aqueous suspension concentrate formulation for plant protection, comprising:
    a) 15 to 40% by weight, based on the total weight of the formulation, of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide in the form of its crystalline anhydrate;
    b) 0.1 to 10% by weight, based on the total weight of the formulation, of at least one non-ionic surfactant selected from polyoxyethylene-polyoxy-$C_3$-$C_4$-alkylene block copolymers;
    c) 0.1 to 10% by weight, based on the total weight of the formulation, of at least one anionic surfactant comprising at least one arylsulfonate group; and d) 40 to 84.8% by weight, based on the total weight of the formulation, of water;

wherein the pH value of the formulation is in the range of 4 to 6.

2. The aqueous suspension concentrate formulation of claim 1, wherein the component b) is a polyoxyethylene-polyoxypropylene-block copolymer.

3. The aqueous suspension concentrate formulation of claim 1, wherein the ethylene oxide units make up 50% of the alkylene oxide units of polyoxyethylene-polyoxy-$C_3$-$C_4$-alkylene block copolymer.

4. The aqueous suspension concentrate formulation of claim 1, wherein the one or more anionic surfactants of component c) are selected from arylsulfonic acid formaldehyde condensation products.

5. The aqueous suspension concentrate formulation of claim 1 further comprising a water-miscible organic solvent selected from the group consisting of $C_2$-$C_5$-alkanediols and $C_3$-$C_8$-alkanetriols.

6. The aqueous suspension concentrate formulation of claim 5, wherein the solvent is 1,2-propanediol.

7. The aqueous suspension concentrate formulation of claim 5, wherein the weight proportion of the solvent is in the range of from 1 to 20% by weight, based on the total weight of the formulation.

8. The aqueous suspension concentrate formulation of claim 1, further comprising an inorganic dispersant selected from the group consisting of silicic acid, silica, alumina and calcium carbonate.

9. The aqueous suspension concentrate formulation of claim 8, wherein the weight proportion of the dispersant is in the range of from 0.1 to 3% by weight, based on the total weight of the formulation.

10. The aqueous suspension concentrate formulation of claim 1, further comprising a thickener selected from the group consisting of layer silicates, organically modified layer silicates, polysaccharides and heteropolysaccharides.

11. The aqueous suspension concentrate formulation of claim 10, wherein the weight proportion of the thickener is in the range of from 0.05 to 2% by weight, based on the total weight of the formulation.

12. The aqueous suspension concentrate formulation of claim 1, further comprising auxiliaries selected from the group consisting of antifoam agents, preservatives and buffers.

13. A method of controlling undesired vegetation, comprising applying the aqueous suspension concentrate formulation of claim 1, in diluted or undiluted form, to plants, their environment and/or seeds.

14. The method of claim 13, wherein the component b) of the aqueous suspension concentrate formulation is a polyoxyethylene-polyoxypropylene-block copolymer.

15. The method of claim 13, wherein the ethylene oxide units of the aqueous suspension concentrate formulation make up 50% of the alkylene oxide units of polyoxyethylene-polyoxy-$C_3$-$C_4$-alkylene block copolymer.

16. The method of claim 13, wherein the one or more anionic surfactants of component c) of the aqueous suspension concentrate formulation are selected from arylsulfonic acid formaldehyde condensation products.

* * * * *